(12) United States Patent
Buesing

(10) Patent No.: US 7,973,203 B2
(45) Date of Patent: Jul. 5, 2011

(54) METHOD FOR SUBSTITUTING INDENOFLUORENES

(75) Inventor: Arne Buesing, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 399 days.

(21) Appl. No.: 12/096,206

(22) PCT Filed: Nov. 18, 2006

(86) PCT No.: PCT/EP2006/011086
§ 371 (c)(1),
(2), (4) Date: Jun. 5, 2008

(87) PCT Pub. No.: WO2007/068326
PCT Pub. Date: Jun. 21, 2007

(65) Prior Publication Data
US 2008/0319239 A1 Dec. 25, 2008

(30) Foreign Application Priority Data
Dec. 17, 2005 (DE) .......................... 10 2005 060 438

(51) Int. Cl.
C07C 22/00 (2006.01)
C07C 19/08 (2006.01)
C08G 79/08 (2006.01)
H01L 35/24 (2006.01)

(52) U.S. Cl. ............ 570/183; 570/129; 528/8; 528/394; 257/40

(58) Field of Classification Search .................. 570/129, 570/183; 528/8, 394; 257/40
See application file for complete search history.

(56) References Cited

U.S. PATENT DOCUMENTS

| 4,539,507 A | 9/1985 | VanSlyke et al. |
| 5,151,629 A | 9/1992 | VanSlyke |
| 5,840,217 A | 11/1998 | Lupo et al. |
| 6,458,909 B1 | 10/2002 | Spreitzer et al. |

FOREIGN PATENT DOCUMENTS

| EP | 0676461 A2 | 10/1995 |
| EP | 1491568 A1 | 12/2004 |
| WO | WO-98/27136 A1 | 6/1998 |

OTHER PUBLICATIONS

Anemian et al., Monodisperse fluorene oligomers exhibiting strong dipolar coupling interaction, (Chemical Communication, 2002, 15, 1608-1609).*

* cited by examiner

Primary Examiner — Jafar Parsa
(74) Attorney, Agent, or Firm — Connolly Bove Lodge & Hutz LLP

(57) ABSTRACT

The invention relates to a process for the preparation of trans-indenofluorene compounds of the formula (Ia) or cis-indenofluorene compounds of the formula (Ib)

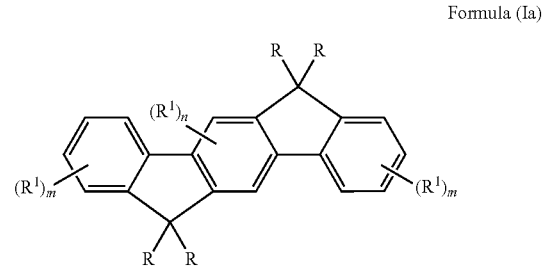

Formula (Ia)

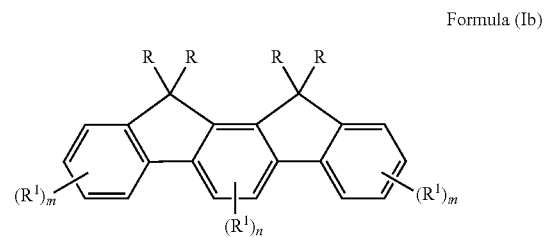

Formula (Ib)

in a reaction with at least one compound of the formula (IIa) or (IIb) respectively

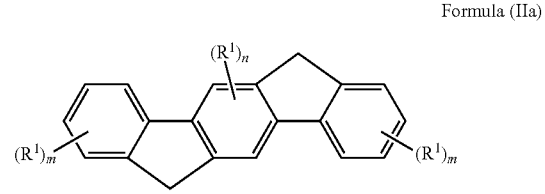

Formula (IIa)

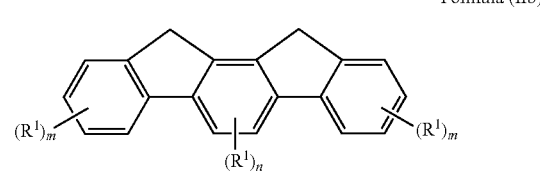

Formula (IIb)

with at least one compound of the R-Hal in the presence of at least one organic base and at least one organic, polar, aprotic solvent.

19 Claims, No Drawings

METHOD FOR SUBSTITUTING INDENOFLUORENES

CROSS-REFERENCE TO RELATED APPLICATIONS

This application is a national stage application (under 35 U.S.C. 371) of PCT/EP2006/011086 filed Nov. 18, 2006, which claims benefit to German application 10 2005 060 438.2 filed Dec. 17, 2005.

BACKGROUND OF THE INVENTION

1. Field of the Invention

The present invention relates to a novel process for the preparation of substituted indenofluorenes, which are used, in particular, in organic, electronic devices.

2. Description of the Prior Art

The use of organic, semiconducting compounds which are capable of emission of light in the visible spectral region in organic electroluminescent devices (OLEDs) is just at the beginning of the market introduction. The general structure of such devices is described, for example, in U.S. Pat. No. 4,539,507, U.S. Pat. No. 5,151,629, EP 0676461 and WO 98/27136.

The organic, semiconducting compounds which are capable of the emission of light in the visible spectral region are, inter alia, also organic compounds and polymers having indenofluorene substructures. In order to improve the applicational properties, it may be advantageous to modify the indenofluorene parent structure, for example by the introduction of suitable substituents.

The prior art discloses processes for the substitution of fluorene parent structures (Kelley et al., *J. Chem. Res. Miniprint* 1997, 12, 2701-2733; Anemian et al., *Chem. Commun.* 2002, 15, 1608-1609), in which an alkylation of a fluorene parent structure is carried out in the presence of potassium tert-butoxide in dimethylformamide (DMF). If this process known from the prior art is applied to indenofluorene parent structures, yields of up to 84% and purities of up to 93% are obtained.

The prior art furthermore discloses a two-step process for the substitution of indenofluorene parent structures (*Macromolecules* 2000, 33, 2016-2020), in which an alkylation of an indenofluorene parent structure is carried out in the presence of n-butyllithium in THF at low temperatures. In this process, purities of up to 99% are achieved; the yield of the two-step process is up to 84%. Owing to the reaction conditions and the reagents selected, the preparation of substituted indenofluorene parent structures is relatively expensive. Furthermore, processes with alkyllithium reagents represent a safety risk on an industrial scale owing to the high combustibility.

There thus continues to be a demand for a process for the preparation of substituted indenofluorene parent structures which on the one hand provides the target compounds in high yield and high purity and on the other hand allows access in an inexpensive and non-critical manner from a safety point of view.

BRIEF DESCRIPTION OF THE INVENTION

Surprisingly, it has now been found that substituted indenofluorene parent structures are accessible in high yield and purity if the substitution is carried out in the presence of selected bases and solvents.

The invention thus relates to a process for the preparation of trans-indenofluorene compounds of the formula (Ia) or cis-indenofluorene compounds of the formula (Ib)

Formula (Ia)

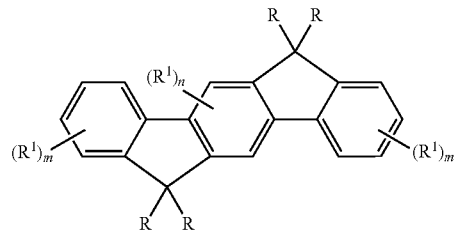

Formula (Ib)

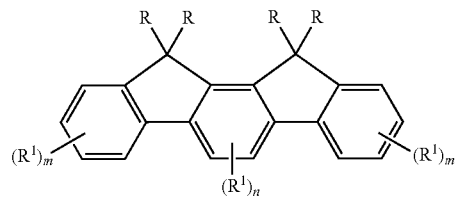

by reaction of at least one compound of the formula (IIa) or (IIb) respectively

Formula (IIa)

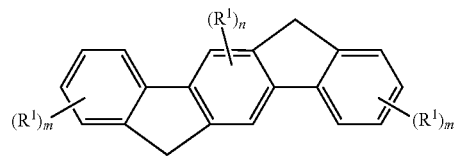

Formula (IIb)

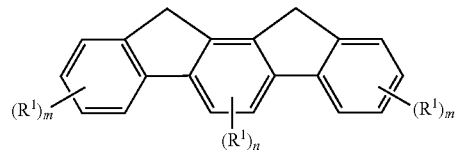

with at least one compound of the formula (III)

R—Hal     formula (III)

in the presence of at least one organic base and at least one organic, polar, aprotic solvent.

The index n stands, independently of one another, for an integer 0, 1 or 2.

The index m stands, independently of one another, for an integer 0, 1, 2, 3 or 4.

A DETAILED DESCRIPTION OF THE INVENTION

The invention relates to a process for the preparation of trans-indenofluorene compounds of the formula (Ia) or cis-indenofluorene compounds of the formula (Ib)

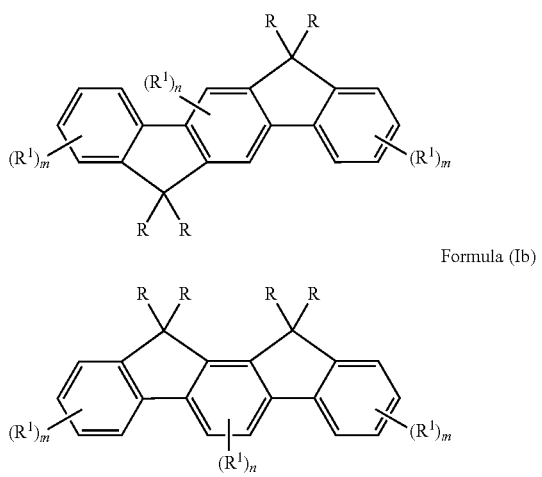

Formula (Ia)

Formula (Ib)

which comprises reacting at least one compound of the formula (IIa) or (IIb) respectively

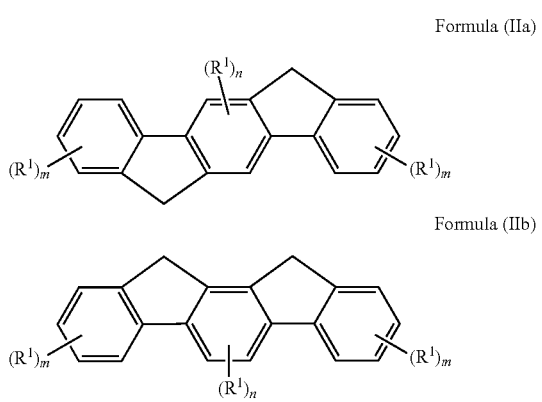

Formula (IIa)

Formula (IIb)

with at least one compound of the formula (III)

R-Hal      formula (III)

in the presence of at least one organic base and at least one organic, polar, aprotic solvent,
wherein
$R^1$ is identical or differ ent on each occurrence and stands for hydrogen, fluorine, chlorine, bromine, iodine, a straight-chain alkyl, alkoxy or thioalkoxy group having 1 to 40 C atoms, a branched alkyl, alkoxy or thioalkoxy group having 3 to 40 C atoms, a cyclic alkyl, alkoxy or thioalkoxy group having 3 to 40 C atoms or an alkenyl group having 2 to 40 C atoms, where the above-mentioned alkyl, alkoxy, thioalkoxy or alkenyl radicals are optionally substituted by one or more radicals $R^2$ and where one or more non-adjacent $CH_2$ groups is optionally replaced by $-R^2C=CR^2-$, $-C\equiv C-$, $Si(R^2)_2$, $Ge(R^2)_2$, $Sn(R^2)_2$, $NR^2$, $C=O$, $P(=O)R^2$, $C=S$, $C=Se$, $C=NR^2$, $-O-$, $-S-$ or $-CONR^2-$ and where one or more H atoms is optionally replaced by F, or an aromatic or heteroaromatic ring system having 5 to 40 aromatic ring atoms, which is optionally substituted by one or more radicals $R^2$, or an aryloxy or heteroaryloxy group having 5 to 40 aromatic ring atoms, which is optionally substituted by one or more radicals $R^2$, or a diarylamino group having 12 to 40 aromatic ring atoms, which is optionally substituted by one or more radicals $R^2$, or a combination of these systems; two or more substituents $R^1$ optionally form a mono- or polycyclic, aliphatic or aromatic ring system, Hal is a leaving group, R is identical or different on each occurrence and stands for a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^2$, where one or more non-adjacent $CH_2$ groups is optionally replaced by $-R^2C=CR^2-$, $Si(R^2)_2$, $Ge(R^2)_2$, $Sn(R^2)_2$, $NR^2$, $C=O$, $C=S$, $C=Se$, $C=NR^2$, $-O-$, $-S-$ or $-CONR^2-$ and where one or more H atoms is optionally replaced by F, or an aromatic or heteroaromatic ring system having 5 to 40 aromatic ring atoms, which is optionally substituted by one or more radicals $R^2$, or an aryloxy or heteroaryloxy group having 5 to 40 aromatic ring atoms, which is optionally substituted by one or more radicals $R^2$, or a combination of these systems, $R^2$ is on each occurrence, identically or differently, H or an aliphatic or aromatic hydrocarbon radical having 1 to 20 C atoms, n is independently of one another, an integer 0, 1 or 2, and m is independently of one another, an integer 0, 1, 2, 3 or 4.

In the compounds of the formulae (Ia), (Ib), (IIa) and (IIb), one or more aromatic carbon atoms may be replaced by heteroatoms, in particular by N.

Furthermore, the compounds of the formulae (Ia), (Ib), (IIa) and (IIb) may carry further substituents $R^1$ which are inert under the reaction conditions on the aromatic parent structure.

These inert substituents $R^1$, which are identical or different on each occurrence, are hydrogen, fluorine, chlorine, bromine, iodine, a straight-chain alkyl, alkoxy or thioalkoxy group having 1 to 40 C atoms, a branched alkyl, alkoxy or thioalkoxy group having 3 to 40 C atoms, a cyclic alkyl, alkoxy or thioalkoxy group having 3 to 40 C atoms or an alkenyl group having 2 to 40 C atoms, where the above-mentioned alkyl, alkoxy, thioalkoxy or alkenyl radicals may be substituted by one or more radicals $R^2$ and where one or more non-adjacent $CH_2$ groups may be replaced by $-R^2C=CR^2-$, $-C\equiv C-$, $Si(R^2)_2$, $Ge(R^2)_2$, $Sn(R^2)_2$, $NR^2$, $C=O$, $P(=O)R^2$, $C=S$, $C=Se$, $C=NR^2$, $-O-$, $-S-$ or $-CONR^2-$ and one or more H atoms may be replaced by F, or an aromatic or heteroaromatic ring system having 5 to 40 aromatic ring atoms, which may be substituted by one or more radicals $R^2$, or an aryloxy or heteroaryloxy group having 5 to 40 aromatic ring atoms, which may be substituted by one or more radicals $R^2$, or a diarylamino group having 12 to 40 aromatic ring atoms, which may be substituted by one or more radicals $R^2$, or a combination of these systems; two or more substituents $R^1$ here may also form a mono- or polycyclic, aliphatic or aromatic ring system, for example a condensed benzo system, with one another.

The radical $R^2$ is on each occurrence, identically or differently, H or an aliphatic or aromatic hydrocarbon radical having 1 to 20 C atoms.

The radical Hal stands for a leaving group, in particular an organic leaving group and/or a halogen atom. Organic leaving groups are preferably taken to mean tosylate, mesylate, trifluoromethanesulfonate, pyridinium, tetraalkylammonium, benzenesulfonate and/or nitrophenolate, halogens are preferably taken to mean Cl, Br and/or I.

The radical R stands for a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may each be replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $-O-$, $-S-$ or $-CONR^2-$ and where one or more H atoms may be replaced by F, or an aromatic or heteroaromatic ring system having 5 to 40 aromatic ring atoms, which may be substituted by one or more radicals $R^2$, or an aryloxy or heteroaryloxy group having 5 to 40 aromatic ring atoms, which may be substituted by one or more radicals $R^2$, or a combination of these systems. The radical R preferably stands for a straight-chain alkyl group having 1 to 20 C atoms or for a branched or cyclic alkyl group having 3 to 20 C atoms, each of which may be substituted by one or more radicals $R^2$, where one or more non-adjacent $CH_2$ groups may each be replaced by $-R^2C=CR^2-$, $-C\equiv C-$, $Si(R^2)_2$, $C=O$, $C=NR^2$, $-O-$, $-S-$ or $-CONR^2-$ and where one or more H atoms may be replaced by F. R particularly preferably stands for a straight-chain, branched or cyclic alkyl group having up to 10 C atoms.

For the radicals R and $R^1$, an aromatic group or heteroaromatic group is preferably taken to mean a system having a common aromatic electron system, where an aryl group contains 6 to 24 C atoms and a heteroaryl group contains 2 to 24 C atoms and in total at least 5 aromatic ring atoms. The heteroatoms are preferably selected from N, O and/or S. For the purposes of this invention, this may be a simple homo- or heterocycle, for example benzene, pyridine, thiophene, etc., or it may be a condensed, aromatic ring system in which at least two aromatic or heteroaromatic rings, for example benzene rings, are "fused" to one another, i.e. are condensed onto one another by anellation, i.e. have at least one common edge and thus also a common aromatic system. These aryl or heteroaryl groups may be substituted or unsubstituted; any substituents present may likewise form further ring systems. Thus, for example, systems such as naphthalene, anthracene, phenanthrene, pyrene, etc., are to be regarded as aryl groups and quinoline, acridine, benzothiophene, carbazole, etc., are to be regarded as heteroaryl groups for the purposes of this invention, while, for example, biphenyl, fluorene, spirobifluorene, etc., do not represent aryl groups for the purposes of this invention since they involve separate aromatic electron systems.

For the purposes of this invention, an aromatic or heteroaromatic ring system is intended to be taken to mean a system which does not necessarily contain only aryl or heteroaryl groups, but instead in which a plurality of aryl or heteroaryl groups may also be interrupted by a short non-aromatic unit (less than 10% of the atoms other than H, preferably less than 5% of the atoms other than H), such as, for example, an $sp^3$-hybridised C, N or O atom. Thus, for example, systems such as 9,9'-spirobifluorene, 9,9-diarylfluorene, triarylamine, diaryl ether, etc., are also intended to be taken to mean aromatic ring systems for the purposes of this invention.

For the purposes of the present invention, a straight-chain $C_1$- to $C_{40}$-alkyl group, a branched alkyl group having 3 to 40 C atoms or a cyclic alkyl group having 3 to 40 C atoms is taken to mean systems in which individual H atoms or $CH_2$ groups may also be substituted by the above-mentioned groups, particularly preferably the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl and octynyl.

A straight-chain $C_1$- to $C_{40}$-alkoxy group, a branched alkoxy group having 3 to 40 C atoms or a cyclic alkoxy group having 3 to 40 C atoms is particularly preferably taken to mean methoxy, ethoxy, n-propoxy, i-propoxy, n-butoxy, i-butoxy, s-butoxy, t-butoxy or 2-methylbutoxy.

An aryl or heteroaryl group, which may be monovalent or divalent, depending on the use, which may in each case also be substituted and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole. For the purposes of this invention, aromatic and heteroaromatic ring systems, in addition to the above-mentioned aryl and heteroaryl groups, are taken to mean, in particular, biphenylene, terphenylene, fluorene, spirobifluorene, dihydrophenanthrene, tetrahydropyrene and cis- or trans-indenofluorene.

Preference is given to compounds in which the symbol $R^1$, identically or differently on each occurrence, stands for H and/or in which at least one symbol $R^1$, identically or differently on each occurrence, stands for a straight-chain alkyl group having 1 to 10 C atoms, preferably 1 to 8 C atoms, or a branched alkyl group having 3 to 10 C atoms, preferably 3 to 8 C atoms, where one or more non-adjacent $CH_2$ groups may be replaced by $-R^2C=CR^2-$, $-C\equiv C-$, $-O-$ or $-S-$ and where one or more H atoms may be replaced by F, or a monovalent aryl or heteroaryl group having 5 to 16 aromatic ring atoms, which may be substituted by one or more radicals $R^2$, particularly preferably for methyl, tert-butyl or a monovalent aryl or heteroaryl group having 4 to 6 C atoms, which may be substituted by one or more radicals $R^2$, or a diarylamino group having 12 to 20 C atoms, which may be substituted by one or more radicals $R^2$.

The organic bases are preferably metal alkoxides, in particular sodium alkoxides and potassium alkoxides. Preference is given to sodium alkoxides and potassium alkoxides having 1 to 8 carbon atoms, in particular tertiary sodium and/or potassium alkoxides. Particular preference is given to sodium tert-butoxide and potassium tert-butoxide. The list of suitable organic bases is not definitive at this point, but instead the term "organic bases" also encompasses other compounds not mentioned at this point which are equally suitable for the process according to the invention.

The organic, polar, aprotic solvents employed are preferably dimethyl sulfoxide (DMSO), N-methylpyrrolidone (NMP), dimethylformamide (DMF), dimethylacetamide, acetonitrile, acetone or butanone, preferably DMSO or DMF, particularly preferably DMSO.

For the purposes of the process according to the invention, the mixing ratio of compounds of the formula (III) to organic base is preferably between 1:10 and 1:1, particularly preferably between 1:6 and 1:3.

The initial concentration of compounds of the formula (IIa) or (IIb) in the solvent is preferably at most 1 M, particularly preferably at most 0.5 M, in particular at most 0.25 M.

The process according to the invention is preferably operated at a temperature in the range from 0° C. to 100° C. In order to complete the reaction, the reaction mixture can be warmed to temperatures of up to 150° C.

For the purposes of the process according to the invention, the base is preferably initially introduced together with the starting compound of the formula (IIa) or (IIb), and the reaction temperature is controlled through the rate of addition of the compound of the formula (III). The compounds of the formula (III) are preferably added at temperatures between 0° C. and 100° C.

The process according to the invention is preferably operated under an inert gas, for example nitrogen or a noble gas, such as, for example, neon or argon. The process is preferably operated under atmospheric pressure. However, it can also be carried out under elevated or reduced pressure.

The reaction is generally complete, depending on the batch size, between 15 and 30 minutes after addition of the reagent R-Hal, although this statement should not be regarded as a restriction of the process.

For the purposes of the process according to the invention, it may be advantageous to accelerate or even set the reaction in motion by means of auxiliaries known per se to the person skilled in the art. Suitable auxiliaries known to the person skilled in the art are the use of ultrasound, microwaves and/or other activations, for example addition of iodide or silver salts.

The polar, aprotic, organic solvents employed for the purposes of the invention should be adequately dried and where necessary also degassed. The residual water content is preferably at most 0.05% by weight of water (determined by the Karl Fischer method).

The process according to the invention enables the preparation of the target compounds of the formula (Ia) or (Ib) in good yield and high purity in an economical manner, even in amounts required commercially.

Furthermore, the reagents used do not represent a safety risk.

The yields in the process according to the invention are preferably at least 90%, based on the starting compound(s) of the formula (IIa) or (IIb) employed.

The compounds prepared by means of the process according to the invention can be used, for example, as monomers or comonomers for the preparation of corresponding conjugated, partially conjugated or non-conjugated polymers, oligomers or also as the core of dendrimers. The polymerisation here is generally carried out via a halogen functionality still to be introduced.

Furthermore, the alkylated compounds can, after introduction of a halogen functionality, be converted by a Hartwig-Buchwaid coupling into aromatic amines, which can be used, for example, as hole-transport materials, or coupled to further aromatic groups by a Suzuki coupling. These compounds can be used, for example, as host for organic dopants.

The invention is explained in greater detail below with reference to working examples, but without being restricted thereby.

EXAMPLES

Example 1

Preparation of tetraoctyl-trans-indenofluorene

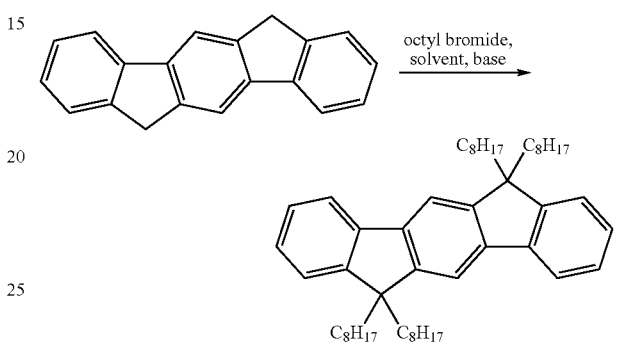

38.7 g (152 mmol) of indenofluorene are dissolved in 600 ml of dried DMSO in a flask which has been dried by heating. 87.8 g (914 mmol) of NaOtBu are added at room temperature. The suspension, which is now blue, is brought to an internal temperature of 80° C. At this temperature, 158 ml (914 mmol) of 1-octyl bromide are added dropwise to the solution, which is now violet, at such a rate that the internal temperature does not exceed 90° C. (duration: about 30 minutes). The batch is held at an internal temperature of 80 to 90° C. for a further 30 minutes, then poured into 1500 ml of ice-water and stirred for about 20 minutes. The precipitated solid is filtered off with suction and washed successively with about 200 ml of $H_2O$ and methanol. The yield is 104.9 g (98%) with an HPLC purity of 99.5%.

Example 2

Preparation of tetramethyl-trans-indenofluorene

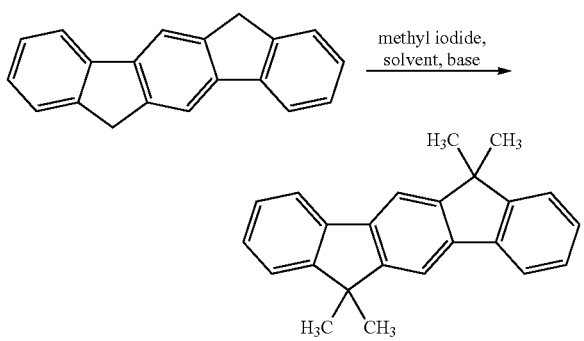

39.0 g (153 mmol) of indenofluorene are dissolved in 1900 ml of dried DMSO in a flask which has been dried by heating. 117.6 g (1224 mmol) of NaOtBu are added at room temperature. The suspension is brought to an internal temperature of 65° C. After 30 min, 76.2 ml (1224 mmol) of MeI in 100 ml of dry DMSO are added dropwise, and the mixture is stirred at this temperature for 7 h. After addition of 100 ml of conc. NH$_4$OH solution, 1500 ml of water are added to the mixture, the solid is filtered off with suction, washed with a total of 2000 ml of water and dried in vacuo. The yield is 45.5 g (96%) with a purity of 99.8%.

Examples 3 to 5

Preparation of tetraoctyl-trans-indenofluorene

The preparation is carried out analogously to Example 1, with the reaction conditions shown in Table 1 being maintained and the results shown in the table being obtained.

TABLE 1

| Example | Conditions (8 equiv. of octyl bromide) | Yield | Purity of crude product |
| --- | --- | --- | --- |
| 3 | KOtBu, DMF, 4 h, 90° C. | 84% | 93% |
| 4 | KOtBu, DMSO, 4 h, 90° C. | 98% | 97% |
| 5 | NaOtBu, DMF, 4 h, 90° C. | 84% | 94% |

Comparative Examples 6 to 8

Preparation of tetraoctyl-trans-indenofluorene

The preparation is carried out analogously to Example 1, with the reaction conditions shown in Table 2 being maintained and the results shown in the table being obtained.

TABLE 2

| Comparative Example | Conditions (8 equiv. of octyl bromide) | Yield | Purity of crude product |
| --- | --- | --- | --- |
| 6 | NaOH 50%, Bu$_4$NBr, 4 d, 90° C. | 25% | 80% |
| 7 | NaH, DMSO, 4 d, 90° C. | 60% | 85% |
| 8 | n-BuLi,[1] THF, −75° C. → RT | 84% | 97% |

[1] Carried out in two cycles

As can be seen from the examples according to the invention and the comparative examples, the process according to the invention gives better yields and higher purities of the crude product than the processes in accordance with the prior art. This applies very particularly if DMSO is used as solvent.

The invention claimed is:
1. A process for the preparation of trans-indenofluorene compounds of the formula (Ia) or cis-indenofluorene compounds of the formula (Ib)

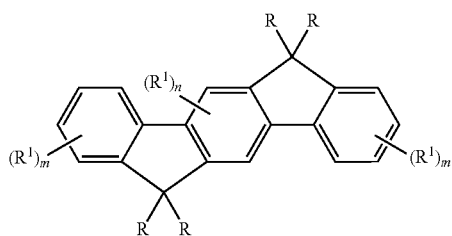

Formula (Ia)

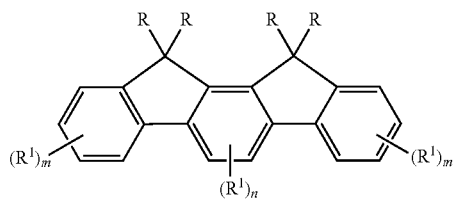

Formula (Ib)

which comprises reacting at least one compound of the formula (IIa) or (IIb) respectively

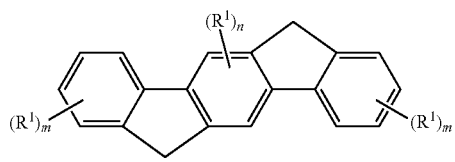

Formula (IIa)

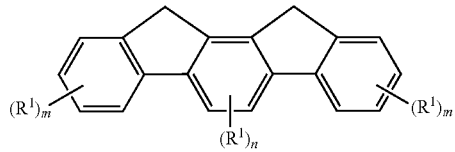

Formula (IIb)

with at least one compound of the formula (III)

R-Hal     formula (III)

in the presence of at least one organic base and at least one organic, polar, aprotic solvent, wherein said organic base is a metal alkoxide, and
wherein
R' is identical or different on each occurrence and stands for hydrogen, fluorine, chlorine, bromine, iodine, a straight-chain alkyl, alkoxy or thioalkoxy group having 1 to 40 C atoms, a branched alkyl, alkoxy or thioalkoxy group having 3 to 40 C atoms, a cyclic alkyl, alkoxy or thioalkoxy group having 3 to 40 C atoms or an alkenyl group having 2 to 40 C atoms, where the above-mentioned alkyl, alkoxy, thioalkoxy or alkenyl radicals are optionally substituted by one or more radicals R$^2$ and where one or more non-adjacent CH$_2$ groups is optionally replaced by —R$^2$C=CR$^2$—, —C≡C—, Si(R$^2$)$_2$, Ge(R$^2$)$_2$, Sn(R$^2$)$_2$, NR$^2$, C=O, P(=O)R$^2$, C=S, C=Se, C=NR$^2$, —O—, —S— or —CONR$^2$— and where one or more H atoms is optionally replaced by F, or an aromatic or heteroaromatic ring system having 5 to 40 aromatic ring atoms, which is optionally substituted by one or more radicals R$^2$, or an aryloxy or heteroaryloxy group having 5 to 40 aromatic ring atoms, which is optionally substituted by one or more radicals R$^2$, or a diarylamino group having 12 to 40 aromatic ring atoms, which is optionally substituted by one or more radicals R$^2$, or a combination of these systems; two or more substituents R$^1$ optionally form a mono- or poly-cyclic, aliphatic or aromatic ring system,
Hal is a leaving group,
R is identical or different on each occurrence and stands for a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^2$, where one or more non-adjacent $CH_2$ groups is optionally replaced by $—R^2C{=}CR^2—$, $—C{\equiv}C—$, $Si(R^2)_2$, $Ge(R^2)_2$, $Sn(R^2)_2$, $NR^2$, $C{=}O$, $C{=}S$, $C{=}Se$, $C{=}NR^2$, $—O—$, $—S—$ or $—CONR^2—$ and where one or more H atoms is optionally replaced by F, or an aromatic or heteroaromatic ring system having 5 to 40 aromatic ring atoms, which is optionally substituted by one or more radicals $R^2$, or an aryloxy or heteroaryloxy group having 5 to 40 aromatic ring atoms, which is optionally substituted by one or more radicals $R^2$, or a combination of these systems, $R^2$ is on each occurrence, identically or differently, H or an aliphatic or aromatic hydrocarbon radical having 1 to 20 C atoms, n is independently of one another, an integer 0, 1 or 2, and m is independently of one another, an integer 0, 1, 2, 3 or 4.

2. The process according to claim 1, wherein Hal is an organic leaving group and/or a halogen atom.

3. The process according to claim 1, wherein said one or more aromatic carbon atoms in the compounds of the formulae (Ia), (Ib), (IIa) and (IIb) are replaced by a heteroatom.

4. The process according to claim 1, wherein said one or more aromatic carbon atoms in the compounds of the formulae (Ia), (Ib), (IIa) and (lib) are replaced by N.

5. The process according to claim 2, wherein said one or more aromatic carbon atoms in the compounds of the formulae (Ia), (Ib), (IIa) and (IIb) are replaced by N.

6. The process according to claim 1, wherein $R^1$ is inert under the reaction conditions.

7. The process according to claim 5, wherein $R^1$ is inert under the reaction conditions.

8. The process according to claim 1, wherein R, identically or differently on each occurrence, stands for a straight-chain alkyl group having 1 to 20 C atoms or for a branched or cyclic alkyl group having 3 to 20 C atoms, each of which is optionally substituted by one or more radicals $R^2$, where one or more non-adjacent $CH_2$ groups is optionally replaced by $—R^2C{=}CR^2—$, $—C{\equiv}C—$, $Si(R^2)_2$, $C{=}O$, $C{=}NR^2$, $—O—$, $—S—$ or $—CONR^2—$ and where one or more H atoms is optionally replaced by F.

9. The process according to claim 7, wherein R, identically or differently on each occurrence, stands for a straight-chain alkyl group having 1 to 20 C atoms or for a branched or cyclic alkyl group having 3 to 20 C atoms, each of which is optionally substituted by one or more radicals $R^2$, where one or more non-adjacent $CH_2$ groups is optionally replaced by $—R^2C{=}CR^2—$, $—C{\equiv}C—$, $Si(R^2)_2$, $C{=}O$, $C{=}NR^2$, $—O—$, $—S—$ or $—CONR^2—$ and where one or more H atoms is optionally replaced by F.

10. The process according to claim 1, wherein said organic bases is sodium alkoxide or potassium alkoxide.

11. The process according to claim 9, wherein said organic bases is sodium alkoxide or potassium alkoxide.

12. The process according to claim 1, wherein the mixing ratio of compounds of the formula (III) to organic base is between 1:10 and 1:1.

13. The process according to claim 11, wherein the mixing ratio of compounds of the formula (III) to organic base is between 1:10 and 1:1 and the initial concentration of compounds of the formula (IIa) or (IIb) in the solvent is at most 1 M.

14. The process according to claim 1, wherein the initial concentration of compounds of the formula (IIa) or (IIb) in the solvent is at most 1 M.

15. The process according to claim 1, wherein the process is operated at a temperature in the range from 0° C. to 100° C.

16. The process according to claim 1, wherein the compound of the formula (III) is added at temperatures between 0° C. and 100° C.

17. The process according to claim 1, wherein the solvent is dimethyl sulfoxide, N-methylpyrrolidone, dimethylformamide, dimethylacetamide, acetonitrile, acetone or butanone.

18. The process according to claim 13, wherein the solvent is dimethyl sulfoxide.

19. The process according to claim 1, wherein the solvent has a residual water content of at most 0.05% by weight of water (determined by the Karl Fischer method).

* * * * *

UNITED STATES PATENT AND TRADEMARK OFFICE
CERTIFICATE OF CORRECTION

PATENT NO. : 7,973,203 B2
APPLICATION NO. : 12/096206
DATED : July 5, 2011
INVENTOR(S) : Arne Buesing It is certified that error appears in the above-identified patent and that said Letters Patent is hereby corrected as shown below:

In the Claims:

At column 10, claim number 1, line number 40, "R'" should read -- $R^1$ --.

Signed and Sealed this
Twenty-seventh Day of September, 2011

David J. Kappos
*Director of the United States Patent and Trademark Office*